United States Patent [19]

McGinnis

[11] 3,987,798
[45] Oct. 26, 1976

[54] TRACHEOSTOMY TUBE AND RETAINER

[75] Inventor: Gerald E. McGinnis, Monroeville, Pa.

[73] Assignee: Lanz Medical Products Corporation, Wilmerding, Pa.

[22] Filed: Mar. 20, 1975

[21] Appl. No.: 560,230

[52] U.S. Cl. ............................. 128/351; 285/192; 128/DIG. 26
[51] Int. Cl.[2] ............... A61M 16/00; A61M 25/02
[58] Field of Search ............... 128/DIG. 26, 351; 285/192

[56] References Cited
UNITED STATES PATENTS

| | | | |
|---|---|---|---|
| 2,908,269 | 10/1959 | Cheng | 128/351 X |
| 3,225,767 | 12/1965 | Smith | 128/351 |
| 3,774,616 | 11/1973 | White et al. | 128/351 X |

Primary Examiner—Channing L. Pace
Attorney, Agent, or Firm—Brown, Murray, Flick & Peckham

[57] ABSTRACT

The proximal portion of a tracheostomy tube extends through an opening in the central body of a retaining member that is held against the front of the neck of a patient. A pair of laterally spaced struts at opposite sides of the opening are connected at one end to the central body. Means rigidly connected to the proximal portion of the tube extend laterally therefrom in opposite directions for connection to the struts extending forward beside the tube, whereby to hold the tube in place.

4 Claims, 4 Drawing Figures

TRACHEOSTOMY TUBE AND RETAINER

After a tracheostomy has been performed on a patient, which means that an opening or stoma has been cut in the front of the neck and the front of the trachea, a tube is inserted through this opening and into the trachea. The upper end or proximal portion of the tube projects forward from the stoma, but the lower end or distal portion of the tube extends down into the trachea. This distal portion of the tube is not perpendicular to the proximal portion, but slants downwardly and rearwardly to follow the slope of the trachea. Therefore, the distance that a tracheostomy tube of any given length will project from a given neck depends upon the elevation at which the stoma is formed. The higher the stoma, the more the projection. Also, the distance from the trachea to the front of the neck varies with different patients, depending on various factors such as the age of the patient and the fatness of the neck. Because the tracheostomy tube may project from necks different distances as just explained, it is necessary to be able to attach the retaining means for the tube to it at different distances from its outer end. The means that have been provided heretofore for this purpose have included a frictional connection between the tube and the retaining member that is tied or strapped around the neck. The trouble with a frictional connection is that mucous, which is very slippery, gets into the connection so that the retaining member often does not hold the tube in the position desired.

It is among the objects of this invention to provide a tracheostomy tube and retaining member of such construction that the outer end of the tube can be held by positive means different definite distances in front of the retaining member and in a simple and easily adjusted manner that also permits the tube to be removed from the throat without disturbing the retaining member.

The preferred embodiment of the invention is illustrated in the accompanying drawings, in which FIG. 1 is a side view of the retainer holding a tracheostomy tube in place;

Figure 1:
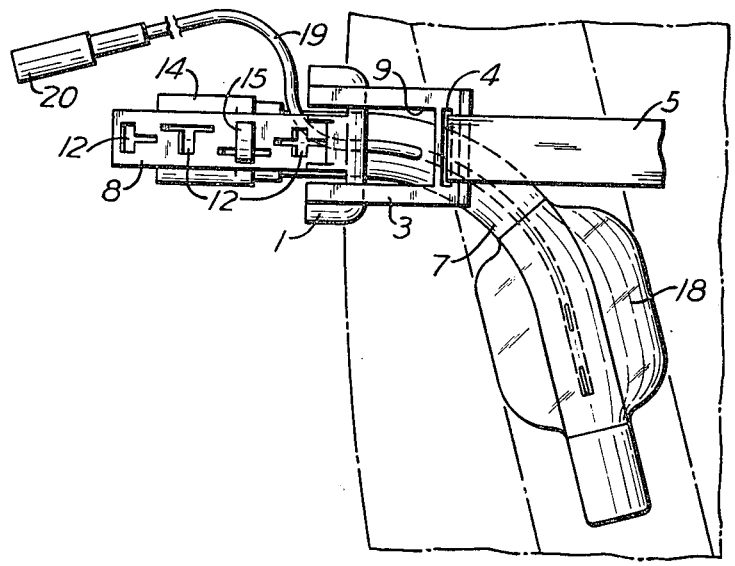

Referring to the drawings, a retaining member for a tracheostomy tube has a central body 1 with an opening 2 through it surrounding the stoma in the front of the neck of a patient who has undergone a tracheostomy operation. Preferably, the opening in the retaining member is considerably larger than the stoma to give ready access to it when it needs to be cleaned out. Also, although the retaining member could be made of metal, it is better to mold it from a plastic. Its central body 1 can be rectangular with upper and lower forwardly extending flanges for strengthening purposes. At the opposite ends of this body, flexible strips 3 that are integral with it extend laterally and may be provided with slots 4 in their outer ends for receiving a band, such as tapes 5 that can be tied against the back of the neck to hold the retaining member in place. A strap can be substituted for the tapes if desired.

Inserted through the stoma and down into the trachea a short distance is a tracheostomy tube 7 having a straight upper or proximal portion and a straight lower or distal portion oblique to each other as is customary. The proximal portion of the tube extends forward from the stoma through the center of the opening 2 in the central body of the retaining member, from which it projects forward a short distance.

Figure 3:
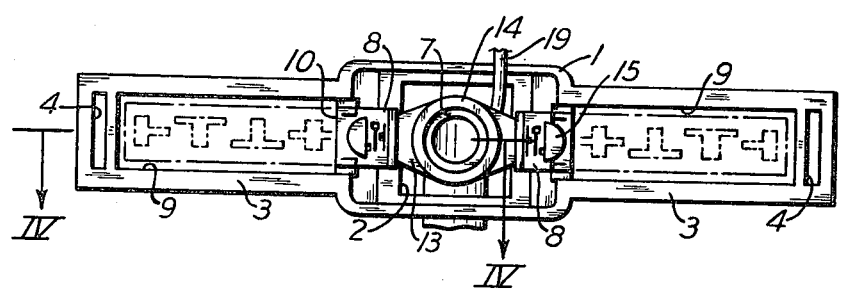
FIG. 3 is a front view of the retainer and tube before put in place.
Figure 2:
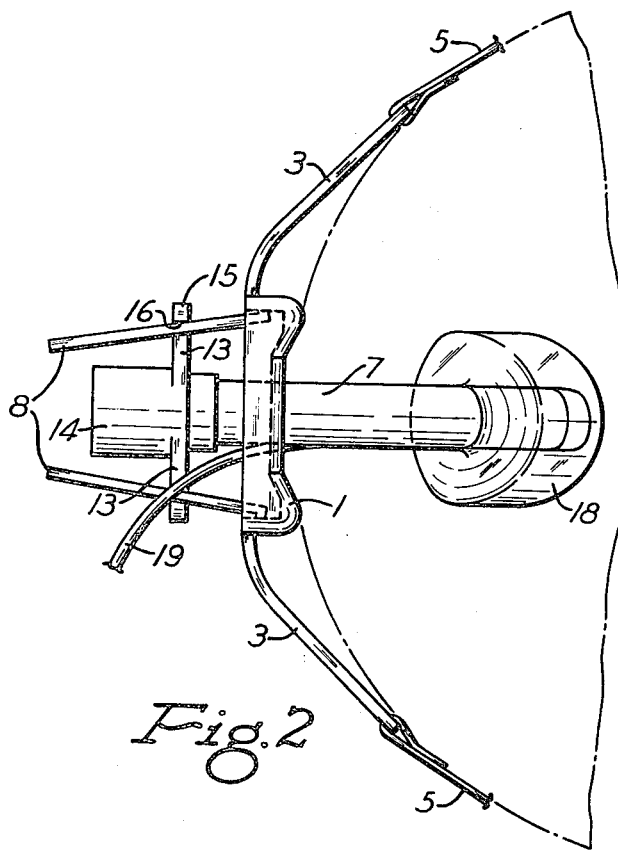
FIG. 2 is a plan view.
Figure 4:
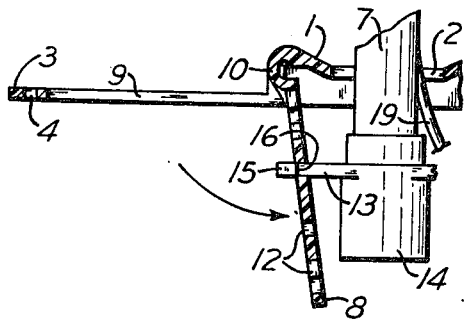
FIG. 4 is a fragmentary horizontal section taken on the line IV—IV of FIG. 3.

It is a feature of this invention that means are provided enabling the proximal end of the tube to be connected to the retaining member in a positive manner and at different predetermined distances from the central body of that member. Accordingly, the retaining member is provided with a strut 8 at each side of its central opening, the struts extending forward along the side between them but spaced from it as shown in FIG. 2. Preferably, the struts are molded integrally with the opposite ends of the central body and, as indicated in dotted lines in FIG. 3, originally lie in openings 9 in strips 3 that the holding tapes are connected to. However, the connections 10 between the inner ends of the struts and the central body are thin enough to permit the struts to be swung forward as shown in FIG. 4.

Each of these struts is provided with a number of longitudinally spaced holes 12 or slots as shown in FIG. 1, those in one strut being directly opposite those in the other strut. These holes are for receiving the outer ends of short arms 13 that project laterally in opposite directions from the end portion of the tube between the struts. The arms are most suitably integral with a short sleeve 14 seated on the outer end of the tube and rigidly attached to it to form a socket. The outer end of each arm is provided with a pointed or rounded head 15 that can be pushed through any one of the holes 12 in the adjoining strut. The holes have walls that stretch or flex enough for that purpose, this being aided by slitting the side walls of the holes. The heads 15 are provided with shoulders 16 that overlap the outer surfaces of the struts to prevent the heads from pulling out of the holes accidentally. However, the struts will yield enough under manual manipulation to permit the heads to be pulled out of the holes.

It will be seen that by inserting the outer ends of the arms 13 into different pairs of holes in the struts, the arms, and therefore the outer end of the tube, can be held different distances from the central body of the retaining member. There is no possibility of this distance being changed unless it is desired to make a change. It cannot change accidentally. Although the struts have some flexibility, they are stiff enough to resist buckling.

The distal portion of the tube inside the trachea may be provided with a conventional inflatable cuff 18 for sealing the space between the tube and the wall of the trachea. The inside of the cuff is connected by a tubule 19 that extends out along the tracheostomy tube 7 to a flexible socket 20, into which air can be forced to inflate the cuff in the usual manner.

According to the provisions of the patent statutes, I have explained the principle of my invention and have illustrated and described what I now consider to represent its best embodiment. However, I desire to have it understood that, within the scope of the appended claims, the invention may be practiced otherwise than as specifically illustrated and described.

I claim:

1. In combination, a tracheostomy tube for insertion in the trachea of a patient through a stoma in the front of his neck and trachea, the tube having a proximal portion for projecting forward from the stoma and a distal portion for extending down inside the trachea, a retaining member having a central body with an opening therethrough for adjustably receiving said proximal portion of said tube, the opposite ends of said central body having means for holding it against the neck of the patient, the retaining member also having a pair of laterally spaced struts at opposite sides of said opening connected at one end to said central body, and tube-holding means rigidly connected to the proximal portion of the tube and extending laterally therefrom in opposite directions for connection to said struts extending forward beside the tube, whereby to hold the tube in place in the retaining member, said struts being provided with means for connecting said tube-holding means to the struts at different selected distances from said central body.

2. In the combination recited in claim 1, each of said struts being provided with a plurality of longitudinally spaced holes for receiving said tube-holding means at different points along from said struts.

3. In the combination recited in claim 2, the walls of said holes being flexible and said tube-holding means being arms with heads at their outer ends larger than said holes for insertion through the holes to hold the arms and struts connected.

4. In the combination recited in claim 3, said struts normally extending laterally away from said central body in opposite directions but being bendable forward into positions extending along said tube for connection with said tube-holding means.

* * * * *